United States Patent [19]

Motomura et al.

[11] 4,342,585

[45] Aug. 3, 1982

[54] METHOD FOR OBTAINING FRUITS HAVING GOOD FLAVOR AND TASTE

[75] Inventors: Yoshie Motomura, Sendai; Jiro Ishiyama; Junichi Shimizu, both of Noda, all of Japan

[73] Assignee: Kikkoman Corporation, Noda, Japan

[21] Appl. No.: 940,600

[22] Filed: Sep. 8, 1978

[30] Foreign Application Priority Data

Sep. 10, 1977 [JP] Japan .................. 52-108346

[51] Int. Cl.³ ............................... A01N 57/00
[52] U.S. Cl. ............................... 71/86; 71/89
[58] Field of Search .......................... 71/86, 89

[56] References Cited

U.S. PATENT DOCUMENTS

| | | | |
|---|---|---|---|
| 3,118,753 | 1/1964 | Shive et al. | 71/92 |
| 4,050,919 | 9/1977 | Motomura et al. | 71/86 |
| 4,209,316 | 6/1980 | McDaniel et al. | 71/86 |

FOREIGN PATENT DOCUMENTS 46-27689  8/1971  Japan .................... 71/92

OTHER PUBLICATIONS

Stoesser et al., "Accumulation of Sugars, etc.;" (1972) CA 77, No. 97598b.
Hartung, "Importance of CAMP and different sugars, etc.;" (1973) CA 79, No. 14323a (1973).
Ghosh et al., "Inhibition of seedling growth, etc.;" (1977) CA 86, No. 151414q (1977).
Motomura et al., "Effects of Cyclic AMP etc.;" (1977) CA 88, No. 116257k (1978).

*Primary Examiner*—Glennon H. Hollrah
*Attorney, Agent, or Firm*—Schuyler, Banner, Birch, McKie & Beckett

[57] ABSTRACT

A method for obtaining fruits having good flavor and taste characterized by treating fruit-bearing flowers, or fruit-bearing flowers and foliar surface and/or developing fruits, or developing fruits and foliar surface with a solution containing cyclic-3',5'-adenylic acid and/or its derivative.

5 Claims, No Drawings

METHOD FOR OBTAINING FRUITS HAVING GOOD FLAVOR AND TASTE

This invention relates to a method for obtaining fruits having good flavor and taste. In particular, it relates to a method for obtaining fruits having good flavor and taste by increasing sugar content, acid content, ester content, etc.

With elevation of the standard in eating life, it is the current trend to demand for fruits having mellowness and good flavor and taste, namely the so-called delicious fruits. In the field of processing fruit, the starting fruits are requested to have high sugar content, high acid content and high ester content in order to improve the quality of juice, fruit vinegar, fruit wine or the like obtainable therefrom.

The factors having the greatest influences upon the flavor and taste of fruits are water content in the soil in the maturing stage, as well as temperature and sunshine hours. Accordingly, any improved technique in tilling and harvesting agricultures and any use of fertilizer or pesticide, which have hitherto been adopted for improving the quality of fruits, cannot be expected to bring about a constant effect under special weather or climatic conditions. Particularly in the dry and continental climate where the atmospheric temperature does not drop even in the night, brewers' grape has a low acid content so that the wine produced therefrom has a light flavor. On the other hand, there is a limit in the breeding of fruits at the present stage, so that it is a technical problem in the art how to improve the quality of fruits, particularly how to increase sugar content, acid content and ester content of fruits with stability.

In view of above, the present inventors have conducted extensive studies to find that, if the fruit-bearing flower (in the case of grape it means the clustery assembly of flowers, while in the case of apple etc., it means clump of flowers, at any stage from the beginning of budding to the finish of flowering), or fruit-bearing flower and foliar surface and/or developing fruit, or developing fruit and foliar surface are treated with a solution containing cyclic-3',5'-adenylic acid (hereinafter referred to as CAMP) and/or CAMP derivative, the difficulties mentioned above are overcome to a great extent and there are obtained mellow and flavorous fluits having increased sugar content, acid content and ester content. This invention has been accomplished on the basis of this finding.

It is an object of this invention to provide fruits having good flavor and taste and a novel method for obtaining said fruits.

Other objects and advantages of this invention will be apparent from the descriptions given below.

Now, this invention will be detailed below.

CAMP usable in this invention includes, for example, CAMP itself namely free CAMP, as well as its alkali metal salts and alkaline earth metal salts (for example, Na salt, K salt, Li salt, Ca salt and the like). CAMP derivatives preferably usable in this invention include 8-derivatives of CAMP (for example, 8-Br-CAMP, 8-I-CAMP, 8-methyl-CAMP and the like), 6-derivatives of CAMP (for example, 6-benzyl-CAMP, 6-allyl-CAMP and the like) and allyl ester derivatives of CAMP (for example, $N^6,O^{2'}$-dibutyl ester-CAMP, $N^6$-butyl ester-CAMP and the like. All these compounds may be used either alone or in combination of two or more members.

The CAMP mentioned above can be produced, for example, by the known fermentative processes and the CAMP derivatives can be produced by the known synthetic processes. Also, they are available commercially.

The solution used for the treatment of this invention is prepared by dissolving CAMP and/or CAMP derivative into a solvent such as water or aqueous alcohol. The treating solution may be used in the form of a mixture with appropriate hydrating agent, emulsifier or spreader, for example, polyoxyethylene-sorbitan monolaurate such as Tween 20, and a mixture of polyoxyethylene dodecyl ether and polyoxyethylene alkylaryl ether such as Aerol OP (manufactured by TOHO Chemicals Ind. Co. Ltd.), Rabiden (manufactured by Nippon Soda K.K.), and Nitten (manufactured by Nissan Kagaku K.K.) or the like. Further, the treating solution may be used in combination with nitrogenous fertilizer or, in some cases, with fungicide or insecticide.

Though the concentration of CAMP and/or CAMP derivative in the treating solution used in this invention varies depending on the kind of fruit or the time of treatment, it is preferably in the range of 1–20,000 ppm in general and the optimum concentration is 100–500 ppm.

Though the time of treatment is somewhat dependent on the kind and variety of fruit, the treatment is preferably carried out in the period from one month before flowering to one month before maturing. Frequency of the treatment may be 1–2 in the above-mentioned preferable period. If desired, however, the frequency may be greater than above.

The treatment may be carried out by an appropriate means such as dipping into the treating solution, spraying with it, coating with it, or the like. The dipping treatment comprises, for example, dipping fruit-bearing flowers or developing fruits into a treating solution containing CAMP and/or CAMP derivative placed in a cup for about 3–10 seconds. The spraying treatment comprises, for example, spraying a treating solution over flower or developing fruit and foliar surface in the form of mist by means of a spray gun. The coating treatment comprises, for example, applying the treating solution by means of brush or the like.

The fruits to which this invention is preferably applicable include citri, grapes including European, American and old varieties, apple, cherry, apricot, pear, peach, tomato, strawberry, melon, watermelon, pumpkin and the like.

If the treatment of this invention is practised upon these fruits in combination with the conventional seedless fleshy technique, the effect of this invention is not affected by it. Further, if a flower cluster of grape is treated according to this invention with a solution of CAMP and/or CAMP derivative, at an appropriately selected treatment concentration and treatment time, in combination with the seedless fleshy technique, the seedless-fleshy grape increases the weight per one berry, making contrast to the generally known fact that a grape simply treated by the conventional seedless fleshy technique is smaller than an untreated grape in the weight per one berry.

Furthermore, the flavor and taste of grape can additionally be increased if an adenine derivative such as 6-benzyladenine, 6-allyladenine or the like is added to the treating solution of this invention at a concentration of 0.1–10,000 ppm.

As above, according to this invention, the matured fresh fruits, such as the fruit of grape, have much higher sugar content, acid content and ester content as compared with conventional fruits, so that the fruits obtained are mellow, excellent in flavor and taste and valuable commercially. Furthermore, the fruits, such as grape, thus obtained can be processed into juices, fruit vinegars, fruit wines, etc. of quite high quality.

CAMP is a sort of nucleotide. As the analogs of CAMP, 2'-, 3'- and 5'-adenylic acids are known. However, CAMP itself is quite different from the analogs in physiological action. For example, 2'-, 3'- and 5'-adenylic acids are known to stimulate the germination of fruit plant pollens [Japanese Patent Kokai (Laid-Open) No. 26517/1973], whereas CAMP and its derivatives have been verified to have an inhibitory action on the germination of fruit plant pollens similarly to gibberellin, benzyladenine and the like. This point will be explained by referring to the following experimental example.

EXPERIMENTAL EXAMPLE 12-year old Campbell Early grape plants were set to have 10 flower clusters per one plot 12 days before the expected flowering day. Three plots were provided as shown in Table 1. Each of the treating solutions was placed in a beaker, into which one flower cluster was dipped at once. The flower cluster was shaken in the beaker several times, and the total dipping time was about 5 seconds per one flower cluster. Afterwards, at the time of flowering, pollens were collected from individual plots, and their germination percentages were determined as mentioned below according to the hanging-drop method of Olmo H. P. [Proceedings of the American Society of Horticultural Science, 41, 219–224 (1942)].

Collection of pollen was carried out at about 11 o'clock a.m. A flower ear was lightly struck onto a glass plate, a small quantity of pollen remaining on glass plate was collected with brush and transferred onto a cover glass, it was wet with one drop of 20% sucross solution by means of micropipette, the cover glass was turned over and placed on a whole slide glass, the surroundings were sealed with liquid paraffin, and then it was left standing at 25° C. for 6 hours, after which the germination percentage was measured.

The number of pollen particles tested was in the range of 400–1500 per one treatment. Pollen particles of which pollen tube reached a length twice or more the diameter of particle were regarded as germinated.

Germination percentage was determined for all the 10 flower clusters belonging to each plot, which were averaged plot by plot and shown in Table 1.

TABLE 1

| No. | Treating solution | | Germination percentage of pollen |
|---|---|---|---|
| 1 | Tween 20 | 100 ppm | 8.2 |
|   | CAMP | 200 ppm | |

TABLE 1-continued

| No. | Treating solution | | Germination percentage of pollen |
|---|---|---|---|
| 2 | Tween 20 | 100 ppm | 5.3 |
| 3 | Gibberellin | 100 ppm | 55 |
|   | Tween 20 | 100 ppm | |

This invention will be illustrated more concretely with reference to the following examples, but the invention is not limited thereto.

EXAMPLE 1

10-year old grape trees belonging to the varieties shown in Table 2 were used as test plants. They were treated with a 200 ppm aqueous solution of CAMP-Na salt (A) 13 days before the flowering, (B) 15 days after the flowering, or (C) 13 days before the flowering and 15 days after it, each once.

Delaware and Campbell Early were dipped into the treating solution in a beaker. Muscat Bailey A, Niagara, Semillon, Riesling, Koshu, Cabernet Sauvignon, Chardonnay, Zenkoji and Black Queen were treated by means of spray gun. Concord was treated by coating by means of brush. The dipping and coating treatments were carried out over flower cluster or developing fruits, while the spraying treatment was carried out over flower cluster and foliar surface or over developing fruit and foliar surface. The number of flower clusters was 10 per one plot. After full maturity, all the 10 fruit clusters were freed from diseased berries and all the remaining berries were crushed with juicer. The juice obtained was filtered through a filter paper, and the filtrate was devoted to the analyses of sugar and acid. By a panel consisting of 20 organoleptic specialists, a two-point taste comparison test was carried out with the untreated plot (D) as control. The number of persons who judged the flavor and taste agreeable was as shown in the column of organoleptic test. The results are summarized in Table 2.

The sugar analysis was carried out by the full-automatic liquid chromatography of Y. C. Lee et al. [Y. C. Lee, J. F. McKeluy and D. Lang: Anal. Biochem., 27, 567 (1969)] with an apparatus manufactured by Nihon Densi K.K. The acid content was analyzed in the following manner according to the OIV official method [Untersuchungsvorschriften des internationalen Amtes fur Rebe und Wein (CIV)].

Thus, 10 g of juice sample was weighed out and diluted with distilled water to a volume of 100 ml. Using a pH meter, 20 ml of the dilution was titrated up to neutrality of pH 7.0 with 0.1 N NaOH. Assuming that 1 ml of the 0.1 N NaOH corresponded to 0.0075 g of tartaric acid, the consumption of 0.1 N NaOH was converted to the quantity of tartaric acid present in 100 g of sample juice.

TABLE 2

| Variety | Treatment | Reducing sugar (%) | Glucose (%) | Fructose (%) | Sucrose (%) | Acid (%) | Organoleptic test |
|---|---|---|---|---|---|---|---|
| Delaware | A | 16.82 | 6.53 | 9.54 | 0.14 | 2.04 | 18 |
|  | B | 17.35 | 6.89 | 10.11 | 0.13 | 1.8 | 17 |
|  | C | 19.62 | 8.54 | 11.12 | 0.10 | 1.7 | 20 |
|  | D | 14.25 | 6.13 | 7.34 | 0.13 | 0.62 | |
| Campbell Early | A | 15.72 | 7.13 | 8.00 | 0.14 | 1.64 | 19 |
|  | B | 15.54 | 7.07 | 8.16 | 0.14 | 1.52 | 19 |
|  | C | 17.55 | 7.34 | 10.10 | 0.03 | 1.34 | 20 |
|  | D | 12.13 | 6.30 | 5.32 | 0.33 | 0.82 | |

TABLE 2-continued

| Variety | Treatment | Reducing sugar (%) | Glucose (%) | Fructose (%) | Sucrose (%) | Acid (%) | Organoleptic test |
|---|---|---|---|---|---|---|---|
| Muscat Bailey A | A | 13.88 | 6.21 | 7.56 | 0.10 | 1.34 | 17 |
|  | B | 13.22 | 5.86 | 7.44 | 0.07 | 1.45 | 18 |
|  | C | 15.03 | 6.71 | 8.67 | 0.06 | 1.27 | 19 |
|  | D | 11.7 | 5.23 | 5.11 | 0.05 | 0.62 |  |
| Niagara | A | 12.22 | 5.89 | 5.67 | — | 1.03 | 20 |
|  | B | 11.70 | 6.00 | 5.79 | — | 1.20 | 20 |
|  | C | 13.12 | 6.34 | 6.12 | — | 0.93 | 20 |
|  | D | 9.92 | 5.26 | 4.31 | — | 0.60 |  |
| Concord | A | 12.97 | 4.98 | 7.86 | — | 1.83 | 19 |
|  | B | 13.17 | 4.98 | 7.87 | — | 1.54 | 20 |
|  | C | 14.63 | 5.75 | 8.34 | — | 1.80 | 20 |
|  | D | 8.74 | 4.35 | 4.22 | — | 0.71 |  |
| Semillon | A | 12.78 | 5.78 | 6.31 | 0.03 | 1.32 | 19 |
|  | B | 13.52 | 5.94 | 6.82 | 0.05 | 1.42 | 20 |
|  | C | 13.78 | 6.38 | 7.00 | 0.04 | 1.24 | 20 |
|  | D | 9.98 | 5.25 | 4.32 | 0.03 | 0.74 |  |
| Riesling | A | 12.57 | 3.67 | 8.48 | 0.42 | 1.38 | 20 |
|  | B | 13.71 | 4.11 | 8.88 | 0.60 | 1.45 | 20 |
|  | C | 15.33 | 4.56 | 9.78 | 0.52 | 1.37 | 20 |
|  | D | 10.27 | 3.53 | 6.13 | 0.34 | 0.63 |  |
| Koshu | A | 12.83 | 6.78 | 5.07 | 0.33 | 1.11 | 20 |
|  | B | 12.84 | 6.77 | 6.05 | 0.27 | 1.17 | 20 |
|  | C | 14.77 | 7.60 | 6.11 | 0.34 | 1.06 | 20 |
|  | D | 11.39 | 6.78 | 4.46 | 0.23 | 0.52 |  |
| Cabernet Sauvignon | A | 13.41 | 4.77 | 8.99 | — | 1.52 | 19 |
|  | B | 13.06 | 4.87 | 8.13 | — | 1.38 | 19 |
|  | C | 15.71 | 5.32 | 10.00 | — | 1.47 | 19 |
|  | D | 10.23 | 4.24 | 4.75 | — | 0.72 |  |
| Chardonnay | A | 13.97 | 5.11 | 8.64 | 0.35 | 1.42 | 20 |
|  | B | 14.23 | 7.54 | 9.78 | 0.42 | 1.65 | 20 |
|  | C | 16.81 | 5.62 | 10.63 | 0.34 | 1.78 | 20 |
|  | D | 11.21 | 4.53 | 5.32 | 0.25 | 0.85 |  |
| Zenkoji | A | 13.08 | 5.64 | 6.89 | 0.34 | 1.42 | 20 |
|  | B | 13.61 | 6.00 | 7.01 | 0.11 | 1.52 | 20 |
|  | C | 14.77 | 6.32 | 8.11 | 0.21 | 1.60 | 20 |
|  | D | 11.43 | 5.15 | 4.28 | 0.37 | 0.65 |  |
| Black Queen | A | 15.80 | 7.22 | 7.41 | 0.28 | 2.04 | 19 |
|  | B | 15.05 | 7.00 | 7.33 | 0.21 | 2.22 | 19 |
|  | C | 17.87 | 7.18 | 7.70 | 0.34 | 2.45 | 20 |
|  | D | 12.22 | 6.20 | 4.56 | 0.21 | 0.92 |  |

EXAMPLE 2

Using 12-year old Delaware trees, 7 plots were provided as shown in Table 3. Two flower clusters were set per one bearing shoot (new branch), which corresponded to 70 flower clusters per each plot. The flower clusters were treated by spray at a dose of one liter/10 ares.

Fully matured fruits taken from each plot were processed in the same manner as in Example 1, and the resulting juices were subjected to organoleptic test in the same manner as in Example 1.

One liter of each juice obtained above was placed in a 2-necked flask of 5 liter capacity, heated to 50° C., and distilled under a reduced pressure of 15 mm Hg with continuous introduction of nitrogen gas. The distillate was cooled first at 0° C. (with ice water) and then at −70° C. (with dry ice and acetone) to condense the flavor component in the trap. The distillation was continued until 10 ml of flavor component was obtained.

Flavor concentration of the distillate was determined by a panel consisting of 10 specialists by the method of organoleptic test. The determination comprised diluting the distillate until flavor intensity of the dilution became identical with that of 100-fold dilution obtained from the distillate of untreated plot, and determining the dilution factor. The results obtained were as shown in Table 3.

TABLE 3

| Plot No. | Concentration of treating solution and time of treatment | | | The date of harvest | Organoleptic test | Dilution factor of flavor distillate |
|---|---|---|---|---|---|---|
|  | 14 days before flowering | 10 days after flowering | | | | |
|  | *GA (ppm) | *GA (ppm) | CAMP (ppm) | | | |
| 1 | 100 | 100 | — | Aug. 30 | 14 | 80 |
| 2 | 100 | 50 | — | Aug. 30 | 10 | 90 |
| 3 | 100 | 50 | 100 | Aug. 28 | 17 | 120 |
| 4 | 100 | 50 | 500 | Aug. 28 | 18 | 130 |
| 5 | 100 | — | 100 | Sept. 10 | 19 | 140 |
| 6 | 100 | — | 500 | Sept. 10 | 20 | 150 |
| 7 | | Untreated | | Sept. 12 | — | — |

(Note)
The treating solution contained 100 ppm of Tween 20 as a spreader.
*GA means gibberellin.

EXAMPLE 3

15-year old apple trees (each threes of Golden Delicious, Indian and Kokko) were treated by spraying 2 ml of treating solution per one flowers clump. The treating solution contained 500 ppm of CAMP-Na salt and 100 ppm of Tween 20 (spreader). The treatment was carried out 10 days before flowering in plot (A), 10 days after flowering in plot (B), and once 12 days before flowering and once 20 days after flowering in plot (C). Plot (D) was untreated.

Thirty fully matured fruits were taken from each treated and untreated tree, from which juice was taken by means of a juicer. After filtration with filter paper, sugar content of the juice was determined by Bertrand method [Method in Carbohydrate Chemistry, (Dische. Z), Vol. 1, Page 477, Academic Press, New York] and its acid content was determined in the following manner, assuming that the acid was malic acid.

Thus, 5 g of juice was diluted with distilled water to 100 ml, its 20 ml was taken into a 150 ml Erlenmeyer flask, 4 drops of phenolphthalein was added to it, and it was titrated with 0.1 N NaOH. Assuming that 1 ml of 0.1 N NaOH corresponds to 0.0067 g of malic acid, the consumption of 0.1 N NaOH was converted into the quantity of malic acid present in 100 g of juice.

Organoleptic test was carried out in the same manner as in Example 1.

The results obtained were as summarized in Table 4.

TABLE 4

| Variety | Treatment | Sugar (%) | Acid (%) | Organoleptic test |
|---|---|---|---|---|
| Golden Delicious | A | 7.11 | 0.601 | 15 |
| | B | 7.93 | 0.628 | 16 |
| | C | 8.33 | 0.644 | 18 |
| | D | 5.12 | 0.377 | |
| Indian | A | 7.63 | 0.372 | 16 |
| | B | 8.64 | 0.437 | 19 |
| | C | 8.75 | 0.484 | 19 |
| | D | 6.63 | 0.234 | |
| Kokko | A | 8.57 | 0.682 | 17 |
| | B | 9.73 | 0.725 | 17 |
| | C | 10.22 | 0.783 | 19 |
| | D | 7.38 | 0.406 | |

EXAMPLE 4

Using 12-year old Cambell Early grape trees, three plots were provided as shown in Table 5. Eleven days before flowering, two flower clusters were set per one bearing shoot and dipped into the treating solution having the concentration shown in Table 5 in a cup.

Of the fully matured fruits collected from each treated and untreated plot, 10 clusters were devoted to organoleptic test, while the remaining 10 clusters were treated in the same manner as in Example 1 for the sake of analysis. Acid content of juice was analyzed by repeating the procedure of Example 1, while the sugar content was determined with Brix saccharimeter. Taking the sugar and acid contents of untreated plot as controls, the sugar increase percentage and the acid increase percentage in treated plots were determined. Also, a two-point taste comparison test was carried out by the same organoleptic test as in Example 1, using untreated plot as control.

$$\text{Sugar increase percentage (\%)} = \frac{\text{Sugar content of the berry taken from treated tree}}{\text{Sugar content of the berry taken from untreated tree}} \times 100$$

$$\text{Acid increase percentage (\%)} = \frac{\text{Acid content of the berry taken from treated tree}}{\text{Acid content of the berry taken from untreated tree}} \times 100$$

The results obtained are summarized in Table 5, in which average weight of fruit cluster is also given.

TABLE 5

| Plot No. | CAMP (ppm) | Average weight of fruit (g) | Sugar increase percentage (%) | Acid increase percentage (%) | Organoleptic test |
|---|---|---|---|---|---|
| 1 | 300 | 124.9 | 132 | 174 | 20 |
| 2 | 3000 | 157.9 | 158 | 189 | 20 |
| 3 | Untreated | 111.1 | 100 | 100 | |

(Note)
The treating solution contains 100 ppm of Aerol OP (manufactured by TOHO Chemicals Ind. Co. Ltd.) as a spreader.

EXAMPLE 5

Using 12-year old Delaware grape trees, the plots mentioned in Table 6 were provided. Two flower clusters were set per one bearing shoot, and one are was taken as one plot. 14 days before flowering, the flower clusters were sprayed with the treating solution having the concentration shown in Table 6 at a dose of 30 liter per are. 10 days after flowering, a solution containing 50 ppm of gibberellin was again sprayed.

20 fully matured fruit clusters were collected from each treated and untreated plot, of which 10 clusters were devoted to organoleptic test, while the remaining 10 clusters were treated in the same manner as in Example 1 and then analyzed. That is to say, juices were taken from them and their sugar and acid contents were analyzed in the same manner as in Example 4.

The results were as shown in Table 6, in which average weight of fruit cluster, weight per one berry and percentage of seedless fleshy (proportion of the number of seedless-fleshy berries per one fruit cluster to the total berry number per one fruit cluster) were also listed.

TABLE 6

| Plot No. | 14 days before flowering CAMP (ppm) | Average weight of cluster (g) | Seedless fleshy berry rate (%) | Wt. per one berry (g) | Sugar content (%) | Acid content (%) | Harvested date |
|---|---|---|---|---|---|---|---|
| 1 | 100 | 94.0 | 0.9 | 1.78 | 126 | 198 | Sept. 11 |
| 2 | 500 | 121.4 | 0.8 | 1.89 | 127 | 227 | Sept. 11 |
| 3 | Untreated | 150.3 | 0.3 | 2.18 | 100 | 100 | Sept. 11 |

(Note)
The treating solution contains 100 ppm of Aerol OP as a spreader.

EXAMPLE 6

8-year old Muscat Bailey A grape trees were used. 8 days before flowering, flower clusters and foliar surface were sprayed with 1000 ppm CAMP solution containing 100 ppm of Aerol OP as spreader at a rate of 300 liters/10 ares. 20 days after flowering, the fruits and foliar surface were sprayed with 100 ppm CAMP solution containing 100 ppm Aerol OP at a rate of 300 liters/10 ares. One month after it, fruits and foliar surface were again sprayed with the same CAMP solution at a rate of 500 liters/10 ares.

Diseased berries were rejected from the collected fruit, and juice was taken from the remainder with desprouting crusher.

As compared with untreated plot, the increases in juice yield, sugar content (measured with Brix saccharimeter) and acid content (measured by the official method) found in treated plot were 50%, 32% and 110%, respectively.

Then, a wine was brewed from this juice. Thus, the juice was fermented in the usual manner by the use of *Saccharomyces cerevisiae* var. *ellipsoides* as a yeast, after which it was after-fermented, cooled and aged to give a wine. The juice obtained from the untreated plot was similarly processed to give a wine. The wines thus obtained were subjected to organoleptic test (two-point taste comparison test) by a panel consisting of 10 specialists. As the result, 10 of the 10 persons judged the wine produced from the grape of treated plot to be solemn and excellent.

Also, the components of the juices were analyzed. Sugar was analyzed in the same manner as in Example 1. Acid was analyzed by the usual gas chromatographic method [Journal of the Association of Official Analytical Chemists, Vol. 53, Page 17 (1970)].

The results obtained were as summarized in Table 7.

TABLE 7

| | | Glucose (%) | Fructose (%) | Tartaric acid (%) | Malic acid (%) | Lactic acid (%) |
|---|---|---|---|---|---|---|
| Juice | Treated | 10.61 | 16.73 | 0.32 | 0.34 | — |
| | Untreated | 8.51 | 13.12 | 0.30 | 0.15 | — |
| Wine | Treated | 5.28 | 6.25 | 0.28 | 0.08 | 0.50 |
| | Untreated | 3.67 | 4.28 | 0.20 | — | 0.21 |

EXAMPLE 7

Using 10-year old Muscat Bailey A grape trees, 9 plots were provided as shown in Table 8. Two flower clusters were set per one bearing shoot, which was corresponded to 20 flower clusters per each plot. In treated plots No. 1 to No. 8, the clusters were dipped in the treating solution having the concentration shown in Table 8 in a cup.

Twenty fully matured fruit clusters were collected from each treated and untreated plot and processed in the same manner as in Example 1. The juice obtained was analyzed for acid by repeating the procedure of Example 1 and for sugar content by means of Brix saccharimeter, from which acid increase percentage and sugar increase percentage were determined. The results were as summarized in Table 8, in which the average weight of fruit cluster is also mentioned.

TABLE 8

| | Concentration of treating solution and time of treatment | | | | | | | |
|---|---|---|---|---|---|---|---|---|
| | 12 days before flowering | | 10 days after flowering | | Average weight of cluster (g) | Sugar increase percentage (%) | Acid increase percentage (%) | The date of harvest |
| Plot No. | GA (ppm) | CAMP derivative (ppm) | GA (ppm) | CAMP derivative (ppm) | | | | |
| 1 | 100 | | 100 | | 187 | 105 | 91 | Sept. 5 |
| 2 | | A200 | 100 | | 195 | 137 | 153 | Sept. 3 |
| 3 | | A200 | 100 | A200 | 198 | 132 | 164 | Sept. 3 |
| 4 | | A200 | | A200 | 352 | 148 | 210 | Sept. 18 |
| 5 | | B100 | 50 | B 20 | 198 | 121 | 159 | Sept. 3 |
| 6 | 100 | | | B 50 | 188 | 134 | 112 | Sept. 5 |
| 7 | | B100 | | B100 | 345 | 150 | 190 | Sept. 18 |
| 8 | 100 | | | C100 | 185 | 130 | 170 | Sept. 4 |
| 9 | | | Untreated | | 256 | 100 | 100 | Sept. 20 |

(Note)
(1) In Table 8, A, B and C denote the following:
A: 8-methyl-CAMP
B: 6-benzyl-CAMP
C: dibutyl-CAMP
(2) The treating solution contains 100 ppm of Aerol OP as a spreader.

What is claimed is:

1. A method for obtaining fruits having good flavor and taste which consists essentially of contacting a member selected from the group consisting of fruit-bearing flowers before flowering, and fruits before being harvested, said fruit being selected from the group consisting of apple, tomato, and strawberry, with an effective amount of an aqueous solution containing at least one cyclic-3', 5'-adenylic acid compound selected from the group consisting of cyclic-3', 5'-adenylic acid, alkali metal salts of cyclic-3',5'-adenylic acid, and derivatives of cyclic-3',5'-adenylic acid, said cyclic-3',5'-adenylic acid being present in the concentration of 20 to 3000 p.p.m., and said derivatives of cyclic-3',5'-adenylic acid being selected from the group consisting of 6-benzyl-cyclic-3',5'-adenylic acid, 6-allyl-cyclic-3',5'-adenylic acid, 8-bromo-cyclic-3'5'-adenylic acid, 8-iodine-cyclic-3',5'-adenylic acid, $N^6$, $O^2$-(dibutyl ester)-3',5'-adenylic acid and $N^6$-(butyl ester)-cyclic-3'5'-adenylic acid.

2. A method according to claim 1, wherein said cyclic-3',5'-adenylic acid compound is an alkali metal salt and said alkali metal salt is selected from the group consisting of sodium, potassium and lithium.

3. A method according to claim 2, wherein said cyclic-3',5'-adenylic acid compound is the sodium salt of cyclic-3',5'-adenylic acid.

4. A method according to claim 1, wherein said cyclic-3',5'-adenylic acid compound is cyclic-3',5'-adenylic acid.

5. A method according to claim 1, wherein said contact with said solution is carried out by dipping, spraying, or brushing.

* * * * *